United States Patent [19]

Krass

[11] Patent Number: 4,634,464

[45] Date of Patent: Jan. 6, 1987

[54] DEFOLIANT METHOD

[75] Inventor: Dennis K. Krass, Canal Fulton, Ohio

[73] Assignee: PPG Industries, Inc., Pittsburgh, Pa.

[21] Appl. No.: 678,121

[22] Filed: Dec. 4, 1984

Related U.S. Application Data

[60] Continuation-in-part of Ser. No. 373,815, Apr. 30, 1982, abandoned, which is a division of Ser. No. 136,171, Apr. 15, 1980, Pat. No. 4,344,789, which is a continuation-in-part of Ser. No. 38,043, May 11, 1979, abandoned.

[51] Int. Cl.$^4$ .................... A01N 37/50; A01N 37/34
[52] U.S. Cl. ........................................ 71/70; 71/72; 71/105; 71/111
[58] Field of Search ............... 71/70, 72, 105, 111

[56] References Cited

U.S. PATENT DOCUMENTS

| | | | |
|---|---|---|---|
| 4,046,798 | 9/1977 | Bayer et al. | 71/105 |
| 4,164,410 | 8/1979 | Theissen | 71/111 |
| 4,221,581 | 9/1980 | Rohr et al. | 71/70 |
| 4,324,579 | 4/1982 | Farge et al. | 71/70 |
| 4,497,745 | 2/1985 | Martin | 71/111 |
| 4,551,171 | 11/1985 | Theissen | 71/111 |

Primary Examiner—Richard L. Raymond
Assistant Examiner—R. Lelkes
Attorney, Agent, or Firm—Edward J. Whitfield

[57] ABSTRACT

This invention relates to the use of certain diphenyl ether oxime derivatives as pre-harvest crop defoliants.

3 Claims, No Drawings

DEFOLIANT METHOD

CROSS-REFERENCE TO RELATED APPLICATION

This application is a continuation-in-part of copending application Ser. No. 373,815 filed Apr. 30, 1982, now abandoned, which is a division of application Ser. No. 136,171 filed Apr. 15, 1980, now U.S. Pat. No. 4,344,789, which is a continuation-in-part of application Ser. No. 38,043 filed May 11, 1979, since abandoned.

BACKGROUND OF THE INVENTION

Chemicals are commonly used in a variety of agricultural applications as, for example, terrestrial or aquatic herbicides, growth regulators, antidotes, harvest aids and the like. A defoliant is one such harvest aid and is applied to a crop prior to harvest to promote earlier maturity, reduce bruising, minimize trash and generally enhance crop harvestability and enhance quality of the harvested crop.

An agriculturally acceptable defoliant facilitates leaf drop by accelerating the formation of the abcission layer at the leaf axil but does not affect other abcission layers such as those at the base of bolls or other fruiting bodies. An effective defoliant will cause plants to drop their leaves and will not simply dry or shrivel the leaves since undropped, albeit dried or shriveled, leaves cause harvesting problems, i.e., excess trash in the harvested crop, that increases harvesting, storage and processing costs.

A defoliant must be fast working and be effective over a wide range of climatic conditions and should also be "weather fast", i.e., not significantly affected by precipitation. Also a defoliant must be nontoxic, biodegradable and leave no residue on the fruiting body or the soil. In addition, the maturing process or the quality of the fruiting body must not be adversely affected.

DESCRIPTION OF THE INVENTION

This invention concerns a method for defoliating plants. More particularly, this invention is directed to defoliating crop by applying to the crop, prior to harvesting, an effective amount of diphenylether oxime represented by the Formula I:

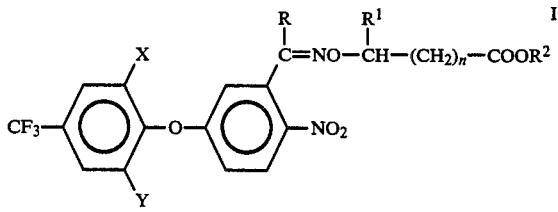

wherein
X and Y are hydrogen or halogen provided that one of X or Y is halogen;
R is hydrogen, halogen, $C_1$ to $C_4$ alkyl or haloalkyl, $C_1$ to $C_4$ alkoxy or alkylthio, mono or dialkylamino, or cyano:
$R_1$ is hydrogen or $C_1$ to $C_4$ alkyl;
$R^2$ is hydrogen or $C_1$ to $C_{10}$ alkyl, haloalkyl or alkoxyalkyl; and
n is 0, 1, 2, or 3.

It is, of course, understood that agronomically acceptable salts of the Formula I compounds are within the scope of this invention, e.g., compounds wherein $R^2$ is an alkali metal ion, ammonium or substituted ammonium ion.

Suitable alkyl radicals of which the various 'R' groups are representative include methyl, ethyl, n-propyl, iso-propyl, n-butyl, t-butyl or iso-butyl. Chloromethyl, chloroethyl, dichloroethyl, bromomethyl, bromoethyl, trifluoromethyl trifluoroethyl, trichloromethyl, and the like are exemplary haloalkyls. As examples of alkoxy and alkylthio radicals there may be mentioned methoxy, ethoxy, propoxy, methylthio, ethylthio or the like. Mono or dialkyl amino groups include methylamino, dimethylamino, methylethylamino, diethylamino or the like. Halogens represented by X, Y, and Z include bromine, chlorine or fluorine. Sodium, potassium or lithium, preferably sodium or potassium, are exemplary or alkali metal ion represented by $R^2$.

Preferred compounds of the Formula I are those wherein X is halogen, e.g., chlorine fluorine or bromine; Y is hydrogen; or halogen; R is alkyl or haloalkyl; $R^1$ is hydrogen; $R^2$ is lower alkyl or haloalkyl; and n is 0. A particularly preferred compound of the Formula I is that wherein X is chlorine, Y is hydrogen, R and $R^2$ are methyl, $R^1$ is hydrogen and n is 0, i.e., the compound 5-(2-chloro-4-trifluoromethylphenoxy)-2-nitroacetophenone oxime-O-(acetic acid, methyl ester); preparation of which is described in Example I of U.S. Pat. No. 4,344,789.

Compounds of the Formula I may be prepared using techniques known to and starting materials available to the art, such as the method described in U.S. Pat. No. 4,344,789. For example, A formula I compound may be prepared by reacting an appropriately substituted diphenyl ether oxime of the Formula II:

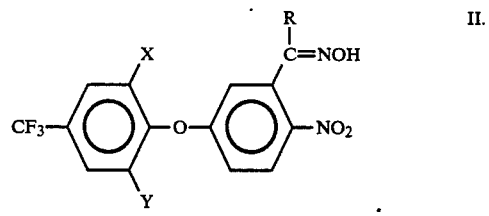

wherein X, Y, and R are as previously defined, with an appropriately substituted haloalkanoic acid or ester of the Formula III:

wherein $R^1$, $R^2$ and n are as previously defined and Hal is halogen, e.g., bromine or chlorine.

The following Example is illustrative of the use of the preferred Formula I compound in the method of this invention.

EXAMPLE

This Example is illustrative of the use of the compound, 5-(2-chloro-4-trifluoromethylphenoxy)-2-nitroacetophenone oxime-O-(acetic acid, methyl ester) as a defoliant for use on cotton according to the method of this invention. Said compound as well as its method of preparation is known to the art and is fully described in U.S. Pat. No. 4,344,789, the disclosure of which is incorporated by reference herein as though fully set forth.

An aqueous solution of said compound was sprayed under prevailing field conditions on test plots of cotton plants at four separate geographic locations at application rates ranging from 0.02 to 0.1 pound per acre. The cotton plants at the time of treatment had attained a mature growth stage, i.e., the bolls had opened, and the crop would be ready for harvest in about 2 to 3 weeks.

At location A, the compound was applied to the test plots at application rates of 0.05, 0.075 and 0.10 pound per acre and the extent of defoliation was evaluated as against an untreated control plot 23 days subsequent to application. Following are the average percent defoliations of four replicate tests at each rate of application at Location A:

| Rate | % Defoliation |
|------|---------------|
| 0.05 | 69 |
| 0.075 | 90 |
| 0.10 | 90 |

At location B, the compound was applied to the test plots at application rates of 0.02, 0.05 and 0.10 pound per acre and the extent of defoliation was evaluated, as against an untreated control plot, 21 days subsequent to application. Following are the average percent defoliations of three replicate tests at each rate of application at Location B:

| Rate | % Defoliation |
|------|---------------|
| 0.02 | 52 |
| 0.05 | 75 |
| 0.10 | 88 |

At Location C, the compound was applied to the test plots at application rates of 0.05, 0.075 and 0.10 pound per acre and the extent of defoliation was evaluated, as against an untreated control plot, 11 days subsequent to application. Following are the average percent defoliations of three replicate tests at each rate of application at Location C:

| Rate | % Defoliation |
|------|---------------|
| 0.05 | 90 |
| 0.075 | 77 |
| 0.10 | 88 |

At Location D, the compound was applied to the test plots at application rates of 0.02, 0.05 and 0.10 pound per acre and the extent of defoliation was evaluated, as against an untreated control plot, 29 days subsequent to application. Following are the percent defoliations of one replicate test at each rate of application at Location D:

| Rate | % Defoliation |
|------|---------------|
| 0.02 | 78 |
| 0.05 | 65 |
| 0.10 | 68 |

At none of the test locations and at none of the rates of defoliant application described in the foregoing was there any indication of boll drop or of damaged bolls.

Although the method of this invention is illustrated in the foregoing Example by the use of a particularly preferred Formula I compound it is believed that other compounds within the scope of Formula I would also be efficacious defoliants. In addition, although the method of this invention is illustrated by pre-harvest defoliation of cotton, the method is equally applicable to other crops that are typically defoliated prior to harvest, such as, for example, soybeans, edible beans and tomatoes.

As to the amount of Formula I compound that can be used in accordance with the method of this invention, the same must, of course, be sufficient to provide the requisite degree of defoliation while not causing substantial damage to the crop. Although the precise amount can readily be determined by routine laboratory or field testing, it is expected that satisfactory pre-harvest crop defoliation can be attained at a rate application in the range of from about 0.05 to about 0.25 pound per acre; although application rates of up to about 0.5 pound per acre could be employed. It is believed that at rates of application of Formula I compound in excess of about 0.5 pound per acre, undesirable crop damage might result.

As to when a Formula I compound is applied in accordance with the method of this invention, typically from a few days, i.e., about 4–6, up to about 3 weeks prior to harvesting the crop ought to provide an acceptable degree of defoliation. Desirably, a Formula I compound is applied in such quantity and at such time prior to harvest so as to provide at least about 70 percent defoliation at the time the crop is harvested.

Of course, Formula I compound used according to this invention can be formulated according to routine methods with any known and commonly used herbicidal diluents, adjuvants or inert carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

If desired, Formula I compound can be formulated or used with other known defoliants to achieve a broader extent of defoliation. Typical defoliants that can be conveniently be combined with Formula I compound include, for example, thidiazuron, merphos, emdothall, 5,5,5-tributylphosphorotrithioate and the like. Typically such formulations will contain from about 5 to about 95 percent by weight of Formula I compound.

The formulations contemplated herein can be applied by any of several methods known to the art. Generally, the formulation will be applied as an aqueous spray. Such application can be carried out by conventional ground equipment, of if desired, the spray can be aerially applied.

Although the invention has been described in considerable detail by the foregoing, it is to be understood that variations may be made therein by those skilled in the art without departing from the spirit and scope thereof as defined by the appended claims.

I claim:

1. A method of defoliating cotton crop prior to harvest thereof while not causing significant damage to the crop by applying to the crop an effective defoliating amount of compound of the formula:

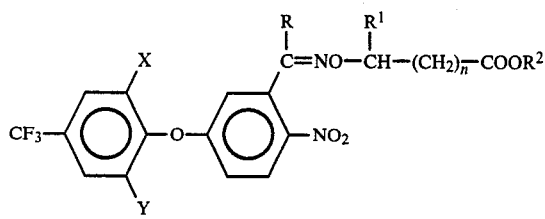

wherein:

X and Y are hydrogen or halogen provided that one of X or Y is halogen;
R is hydrogen, halogen, $C_1$ to $C_4$ alkyl or haloalkyl, $C_1$ to $C_4$ alkoxy or alkylthio, mono or dialkylamino, or cyano:
$R^1$ is hydrogen or $C_1$ to $C_4$ alkyl;
$R^2$ is hydrogen or $C_1$ to $C_{10}$ alkyl, haloalkyl or alkoxyalkyl; and
n is 0, 1, 2, or 3.

2. The method of claim 1 wherein X is halogen; Y is hydrogen; R is alkyl or haloalkyl; $R^1$ is hydrogen; $R^2$ is lower alkyl or haloalkyl; and n is 0.

3. The method of claim 2 wherein the compound is 5-(2-chloro-4-trifluoromethylphenoxy)-2-nitroacetophenone oxime-O-(acetic acid, methyl ester.

* * * * *